Jan. 5, 1960 H. C. SWIM Plant Pat. 1,893
ROSE PLANT
Filed April 2, 1959
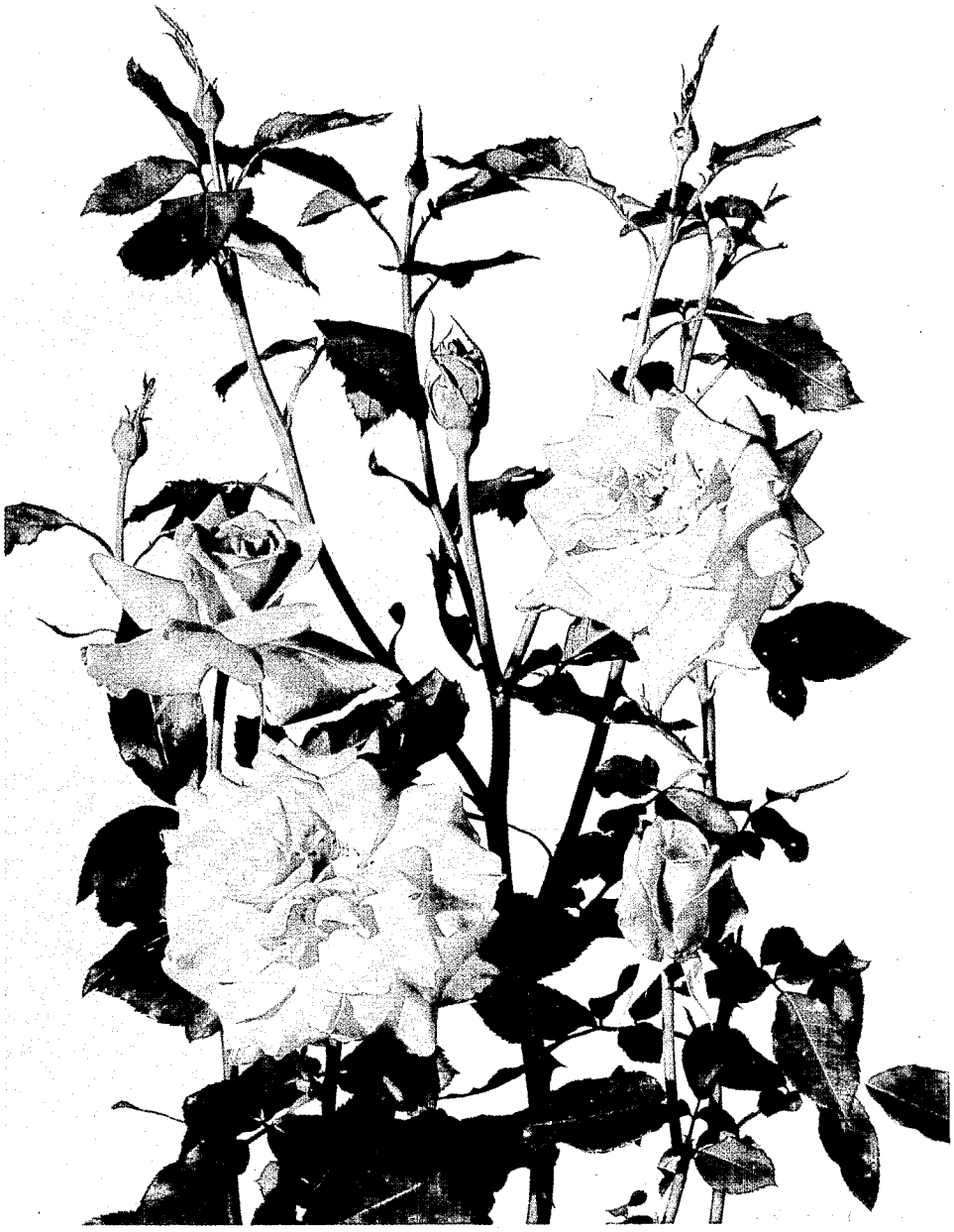
Inventor.
H. C. Swim
By: Robb & Robb
Attorneys.

United States Patent Office

Plant Pat. 1,893
Patented Jan. 5, 1960

1,893

ROSE PLANT

Herbert C. Swim, Ontario, Calif., assignor, by mesne assignments, to C. R. Burr and Company, Inc., Manchester, Conn., a corporation of Connecticut Application April 2, 1959, Serial No. 803,812

1 Claim. (Cl. 47—61)

The present invention relates to a new and distinct variety of rose plant falling between the hybrid tea and floribunda classes (although tending more toward the hybrid tea class), said new variety having been originated by me by crossing the variety "First Love" (Plant Patent No. 921) with the variety "Roundelay" (Plant Patent No. 1,280).

The general objective of this breeding was to produce a new rose variety having characteristics between those of the hybrid tea and floribunda classes, combined with a floriferousness at least equal to or better than either of the parent varieties, a bud form corresponding to that of the parent variety "First Love," but the flowers of which have a greater number of petals, corresponding to that of the parent variety "Roundelay."

A further objective of this breeding was to combine the aforementioned characteristics with a well-formed flower habit, and a habit of bearing flowers of medium size on stems of a suitable length for cutting, and a flower color ranging between pink and red. Still other objectives of this combination included vigorous, attractive and reasonably disease-resistant foliage characteristics. These objectives have been largely achieved, along with other desirable improvements, as evidenced by the following unique combination of characteristics which are outstanding in the new variety and which distinguish it from its parents as well as from all other varieties of which I am aware:

(1) A very vigorous, much-branched, generally upright plant habit;

(2) Attractive, dark green foliage of medium size and of better-than-average disease resistance;

(3) A very floriferous habit, with the flowers borne sometimes singly and sometimes in small clusters on stems of medium length;

(4) Moderately double, medium-sized flowers having better-than-average urn-shaped bud form, with small points at the apices of most petals; and (5) An attractive flower color tonality generally ranging between Rose Madder and Phlox Pink.

In comparison with its seed parent, "First Love," the new variety bears flowers sometimes singly and sometimes in small clusters, as distinguished from the usually singly-borne flower habit of this parent; and the flower color of the new variety is dark pink, while that of the parent variety is relatively light pink.

As compared with its pollen parent, "Roundelay," the flowers of the new variety are less double; and the flower color is dark pink, as distinguished from the dark red flower color of "Roundelay."

Asexual reproduction of my new variety by budding, as performed at Ontario, California, shows that the foregoing characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Robert Ridgeway's Color Standards and Nomenclature (hereinafter abbreviated as "Ridgway"), as indicated:

Type: Bush; outdoor; seedling; for cut flowers and for garden decoration.

Class: Between hybrid tea and floribunda, but tending more toward the hybrid tea class.

Breeding: Seedling.

*Seed parent.*—"First Love."

*Pollen parent.*—"Roundelay."

Propagation: Holds its distinguishing characteristics through succeeding propagations by budding.

*Flower*

Locality where grown and observed: Ontario, California.

Flowers borne: Sometimes singly and sometimes from two to five to stem; in irregular clusters; on stems of normal strength and ranging from medium length to long.

Quantity of bloom: Abundant, outdoors.

Continuity: Nearly continuous during growing season.

Fragrance: From none to slight.

Bud:

*Peduncle.*—From average length to long; average caliper; erect; usually smooth; some stipitate glands and few hairs. Color—near Courge Green, Plate XVII (Ridgway).

*Before calyx breaks.*—Size—medium. Form—medium length; ovoid.

*As calyx breaks.*—Color—between Spiraea Red, Plate 025, page 112 (Wilson) and Erythrite Red, Plate 0027, page 190 (Wilson).

*Sepals.*—Margins of alternate sepals usually with few to several small stipitate glands and none to few slender foliaceous parts; other margins lined with fine, woolly tomentum. Inner surface—with fine, woolly tomentum. Outer surface—usually smooth.

*As first petal opens.*—Size—average. Form—medium length; urn-shaped. Color: outside—between Rose Madder, Plate 23/2, page 23 (Wilson) and Neyron Rose, Plate 623, page 76 (Wilson), inside—between Rose Madder, Plate 23/1, page 23 (Wilson) and Phlox Pink, Plate 625, page 77 (Wilson).

*Opening.*—Opens up well; is not prevented from opening by cold, hot, wet or dry weather.

Bloom:

*Size (when fully open).*—Average; from 3½ inches to 4½ inches.

*Petalage.*—Double; from 18 to 22 petals, plus from 3 to 5 petaloids; arranged regularly.

*Form.*—High-centered at first, but becoming cupped to high-centered; petals being at first somewhat tightly cupped, with tips rolled outward, but becoming later at maturity more loosely flat to cupped; lateral margins of both inside and outside petals sometimes reflexed ½ or more of petal length; apex sometimes reflexed ½ or more of petal length.

Petals:

*Texture.*—Medium thickness. Inside—from satiny to velvety. Outside—satiny.

*Shape.*—Outer—broadly obovate, with apex mucronate; sometimes with 1 or 2 notches. Intermediate—obovate, with apex from rounded to mucronate. Inner—from round to narrowly obovate, with apex from rounded to mucronate.

This description of a newly opened flower was made from a rose grown outdoors in the month of September at Ontario, California:

*Color.*—Outer petal: outside surface—near Phlox Pink, Plate 625/1, page 77 (Wilson); inside surface—near Phlox Pink, Plate 625, page 77 (Wilson). Intermediate petal: outside surface—near Phlox Pink, Plate 625/1, page 77 (Wilson), inside surface—between Rose Madder, Plate 23/1, page 23 (Wilson) and Phlox Pink, Plate 625, page 77 (Wilson). Inner petal: outside surface—between Phlox Pink, Plate 625, page 77 (Wilson) and Phlox Pink, Plate 625/1, page 77 (Wilson); inside surface—between Rose Madder, Plate 23, page 23 (Wilson) and Phlox Pink, Plate 625, page 77 (Wilson).

This description was made from a rose that was open for 3 days outdoors in the month of September at Ontario, California:

*Color.*—Outer petal: outside surface—between Tyrian Rose, Plate 24/3, page 24 (Wilson) and Phlox Pink, Plate 625/2, page 77 (Wilson); inside surface—near Phlox Pink, Plate 625/2, page 77 (Wilson). Inner petal: outside surface—between Phlox Pink, Plate 625/1, page 77 (Wilson) and Phlox Pink, Plate 625/2, page 77 (Wilson); inside surface—between Phlox Pink, Plate 625, page 77 (Wilson) and Phlox Pink, Plate 625/1, page 77 (Wilson).

*General color effect.*—Newly opened flower—between Rose Madder, Plate 23/1, page 23 (Wilson) and Phlox Pink, Plate 625, page 77 (Wilson). 3-days open—between Phlox Pink, Plate 625/1, page 77 (Wilson) and Phlox Pink, Plate 625/2, page 77 (Wilson).

*Behavior.*—Drop off cleanly; not particularly affected by cold, hot, wet or dry weather.

*Flower longevity.*—On bush in garden—4 or 5 days in December. Cut roses grown outdoors and kept at livingroom temperatures—5 days in December.

*Reproductive organs*

Stamens: Average number; arranged regularly about pistils.

Filaments: From medium length to long; from 4 mm. to 12 mm. in length; most with anthers. Color—near Neyron Rose, Plate 023/3, page 76 (Wilson).

Anthers: Medium size; all open approximately at once. Color: upper side—margins near Cadmium Orange, Plate 8/1, page 8 (Wilson); remainder near Canary Yellow, Plate 2/3, page 2 (Wilson); under side—margins near Cadmium Orange, Plate 8/1, page 8 (Wilson); remainder near Canary Yellow, Plate 2/3, page 2 (Wilson).

Pollen: Moderate quantity. Color—near Indian Yellow, Plate 6/2, page 6 (Wilson).

Pistils: Average number; approximately 70 in number.

Styles: Moderately even; from short to average length; from 5 mm. to 10 mm. in length; average caliper; bunched. Color—upper one-half of style near Carmine, Plate 21/3, page 21 (Wilson); remainder near Uranium Green, Plate 63/3, page 63 (Wilson).

Stigma: Color—near Primrose Yellow, Plate 601/2, page 65 (Wilson).

Ovaries: Usually all enclosed in calyx.

Hips: Average length; globular; smooth; walls thick and fleshy. Color (one-half mature)—near Javel Green, Plate V (Ridgway).

Sepals: Falling soon; medium length; straight. Color: inside—near Light Grape Green, Plate XLI (Ridgway); outside—near Absinthe Green, Plate XXXI (Ridgway).

Seeds: From few to average number; from 5 to 10 in number; medium size.

*Plant*

Foliage:

*Leaves.*—Compound of usually 3 to 7 leaflets; from normal abundance to abundant; medium size; leathery and semi-glossy.

*Leaflets.*—Shape—oval, with apex acute. Base—from obtuse to acute. Margin—simply serrate.

*Color.*—Mature: upper surface—near Yew Green, Plate XXXI (Ridgway); under surface—near Deep Grape Green, Plate XLI (Ridgway). Young: upper surface—near Yellowish Olive, Plate XXX (Ridgway), overlaid with near Prussian Red, Plate XXVII (Ridgway), particularly toward margins; under surface—between Cameo Brown, Plate XXVIII (Ridgway) and Walnut Brown, Plate XXVIII (Ridgway).

*Rachis (the supporting stem of the compound leaf).*—Average size. Upper side—grooved; with some small stipitate glands on edges. Under side—smooth; with from none to 4 or 5 small prickles.

*Stipules.*—Medium length; from narrow to medium width; with short to medium length points turning out at an angle of approximately 45°.

*Disease resistance.*—Better-than-average resistance to mildew, as compared with other varieties grown under comparable cultural conditions at Ontario, California.

Growth:

*Habit.*—Bushy; upright; much-branched.

*Growth.*—Very vigorous.

*Canes.*—Heavy.

*Main stems.*—Color—near Olive Green, Plate IV (Ridgway). Large prickles—several; medium length; hooked slightly downward; with medium length, moderately narrow base; color—near Sayal Brown, Plate XXIX (Ridgway). Small prickles—few; color—near Sayal Brown, Plate XXIX (Ridgway). Hairs—none.

*Branches.*—Color—near Biscay Green, Plate XVII (Ridgway). Large prickles—several; medium length; hooked slightly downward; with medium length, moderately narrow base; color—near Mikado Brown, Plate XXIX (Ridgway). Small prickles—few; color—near Mikado Brown, Plate XXIX (Ridgway). Hairs—none.

*New shoots.*—Color—near Courge Green, Plate XVII (Ridgway), with some shadings of near Prussian Red, Plate XXVII (Ridgway). Large prickles—from few to several; from short to medium length; hooked slightly downward; with medium length, moderately narrow base; color—near Corinthian Purple, Plate XXXVIII (Ridgway). Small prickles—few; color—near Corinthian Purple, Plate XXXVIII (Ridgway). Hairs—none.

I claim:

A new and distinct variety of rose plant falling between the hybrid tea and floribunda classes, substantially as herein shown and described, characterized particularly as to novelty by its unique combination of a very vigorous, much-branched, generally upright plant habit, attractive dark green foliage of medium size and of better-than-average disease resistance, a very floriferous habit, with the flowers borne simetimes singly and sometimes in small clusters on stems of medium length, moderately double, medium-sized flowers having better-than- average urn-shaped bud form, with small points at the apices of most petals, and an attractive flower color tonality generally ranging between Rose Madder and Phlox Pink.

No references cited.